(12) United States Patent
Miller

(10) Patent No.: US 8,668,721 B2
(45) Date of Patent: Mar. 11, 2014

(54) CONNECTOR APPARATUS AND METHOD

(75) Inventor: Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 360 days.

(21) Appl. No.: 13/004,694

(22) Filed: Jan. 11, 2011

(65) Prior Publication Data

US 2012/0179205 A1 Jul. 12, 2012

(51) Int. Cl.
A61B 17/70 (2006.01)

(52) U.S. Cl.
USPC .......................................... 606/264

(58) Field of Classification Search
USPC ......... 606/246, 250–253, 264, 265, 267–270, 606/272, 276–279, 301, 324, 330; 403/362; 411/393
See application file for complete search history.

(56) References Cited

U.S. PATENT DOCUMENTS

| 5,047,029 | A | * | 9/1991 | Aebi et al. ..................... 606/264 |
| 5,261,909 | A | * | 11/1993 | Sutterlin et al. ............. 606/264 |
| 5,928,233 | A | * | 7/1999 | Apfelbaum et al. .......... 606/261 |
| 6,551,318 | B1 | | 4/2003 | Stahurski |
| 7,585,312 | B2 | | 9/2009 | Rawlins et al. |
| 2008/0021454 | A1 | | 1/2008 | Chao et al. |
| 2008/0021455 | A1 | | 1/2008 | Chao et al. |
| 2008/0021456 | A1 | | 1/2008 | Gupta et al. |

* cited by examiner

Primary Examiner — Pedro Philogene
Assistant Examiner — David Comstock

(57) ABSTRACT

A spinal stabilization apparatus and method according to which a fastener is engaged with a bone structure of a spinal system. The fastener is connected to a rod by moving the rod downward toward the fastener in a sagittal plane, and the direction of extension of at least a portion of the rod in a coronal plane may be selectively adjusted in predetermined angular increments through 360 degrees.

20 Claims, 11 Drawing Sheets

CONNECTOR APPARATUS AND METHOD

BACKGROUND

The present invention relates in general to spinal systems and in particular to a spinal stabilization apparatus and method utilizing iliac and/or pedicle screws.

To stabilize a spinal system including a spinal column, the extent of displacement between adjacent vertebrae in the spinal column may be reduced, and/or each pair of adjacent vertebrae may be maintained in a desired spatial relationship.

In some cases, rods may be provided that are adapted to extend within the vicinity of the spinal system (including, in some instances, the sacrum and/or adjacent portions of the iliac bones), and connectors may be provided that connect one or more of the rods to one or more of the vertebrae in the spinal system and/or to iliac structures on the pelvis. The rods and connectors may assist in providing immobilization and/or stabilization to the spinal system, and/or may serve as an adjunct to fusion of one or more portions of the spinal system. An example of a system for reducing displacement of a vertebra, in which a rod is employed, is disclosed in U.S. Pat. No. 6,248,107 to Foley et al., the disclosure of which is incorporated by reference.

For spinal stabilization systems that include one or more rods connected to screws or other fasteners attaching the stabilization system to the pelvis, the ability to selectively adjust the direction of extension of at least a portion of one of the rods in a coronal plane may be desired and/or required in order to more easily engage a portion of one of the rods with an iliac fastener, among other desires and/or requirements. As used herein, it is understood that the term "coronal plane" includes any plane of section in the anatomical position that generally passes vertically through the human body and is generally perpendicular to both the median (or sagittal) plane and the horizontal (or axial or transverse) plane, generally dividing the human body into anterior and posterior sections, and further includes any plane of section in the anatomical position that generally passes vertically through the human body, is generally perpendicular to the horizontal (or axial or transverse) plane, and is generally angularly oriented from the median (or sagittal) plane at an angle of orientation ranging from greater than zero degrees up to and including ninety degrees.

Furthermore, as used herein, it is understood that the term "sagittal plane" includes any plane of section in the anatomical position that generally passes vertically through the human body in the prone position and is generally perpendicular to both the coronal plane and the horizontal (or axial or transverse) plane, generally dividing the human body into left and right sections, and further includes any plane of section in the anatomical position that generally passes vertically through the human body in the prone position, is generally perpendicular to the horizontal (or axial or transverse) plane, and is generally angularly oriented from the coronal plane at an angle of orientation ranging from greater than zero degrees up to and including ninety degrees.

SUMMARY OF THE INVENTION

According to one aspect of the present invention, an apparatus for stabilizing a spinal system is provided that includes an extension element adapted to be coupled to a bone structure (including, but not limited to the iliac crest), and a rod-receiver element coupled to the extension element for selectively adjusting the direction of extension of at least a portion of a rod in a first coronal plane, wherein the at least a portion of the rod engages the adjusting means when the rod extends within the vicinity of the spinal system. The rod-receiver element defines a channel having an open top such that at least a portion of the rod may be inserted into the channel by moving the rod in a first sagittal plane. Furthermore, the rod-receiver element may be rotatable 360 degrees in predetermined angular increments in place relative to the extension element to adjust and fix the direction of extension of the at least a portion of the rod in the first coronal plane.

According to another aspect of the present invention, a method of stabilizing a spinal system is provided that includes engaging a fastener with a bone structure, connecting the fastener to a rod extending within the vicinity of the spinal system by moving the rod in a first sagittal plane, and selectively adjusting the direction of extension of at least a portion of the rod in a first coronal plane in predetermined angular increments.

DETAILED DESCRIPTION

Figure 1:
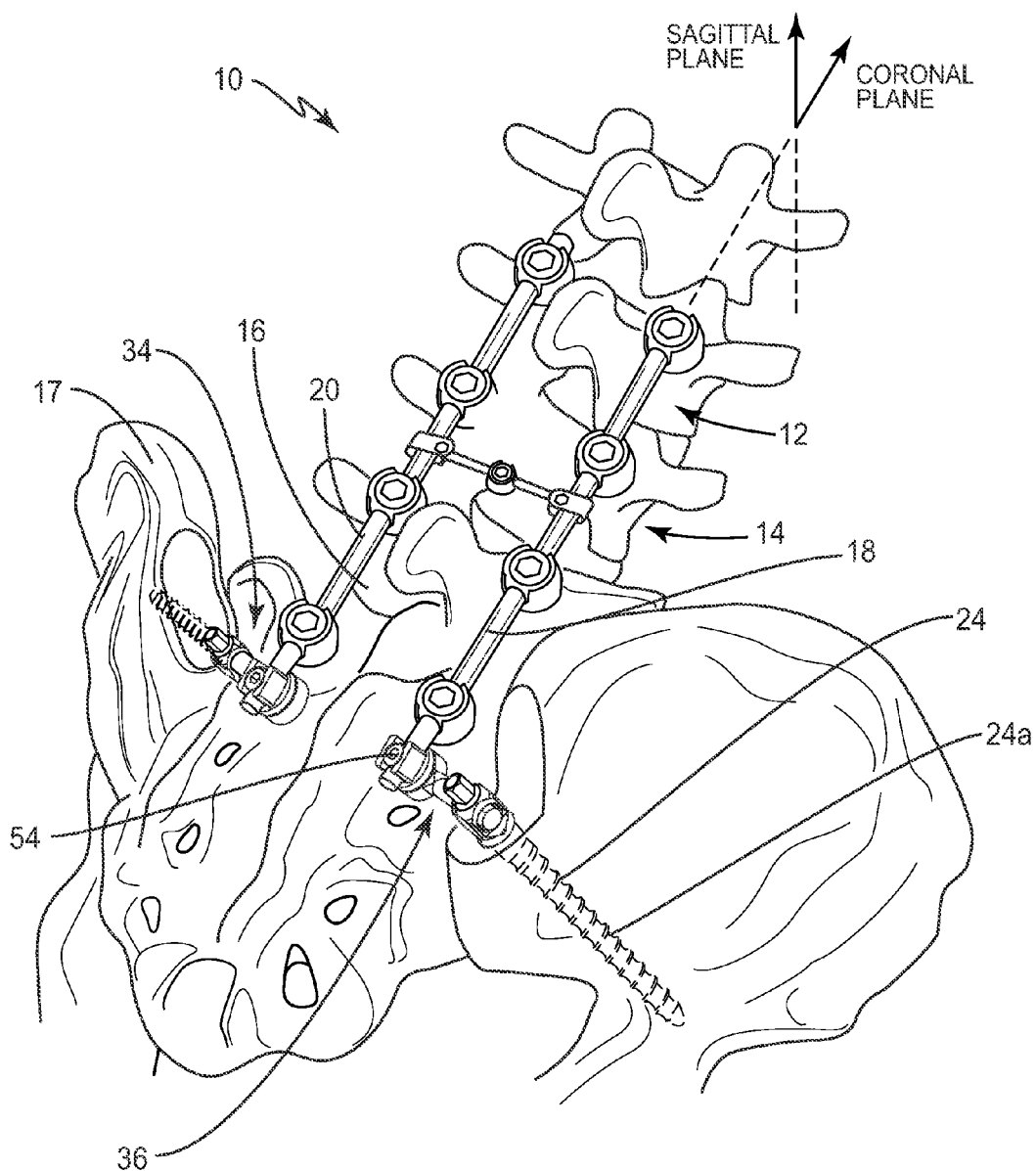
FIG. 1 is a perspective view of a spinal system including vertebral and iliac connectors.

Referring to FIG. 1, a spinal system is generally referred to by the reference numeral 10 and includes vertebrae 12, 14 and 16. It is understood that the spinal system 10 includes a human spinal column composed of various types of vertebrae, of which the vertebrae 12, 14 and 16 are a part, and ligaments and/or other natural and/or artificial structures connected to and/or extending between one or more of the vertebrae. Also shown is an iliac bone structure 17 (such as a portion of the iliac crest, for example) in the vicinity of the spinal system 10. Rods 18 and 20 extend within the vicinity of the spinal system 10 and the iliac bone structure 17 in a spaced relation. Fasteners, in the form of pedicle screws, are threadably engaged with and extend from the right-side pedicles of the vertebrae 12, 14 and 16, respectively. In a like manner, fasteners in the form of pedicle screws are threadably engaged with and extend from the left-side pedicles of the vertebrae 12, 14 and 16. In addition, fasteners, in the form of iliac screws 24 are threadably engaged with and extend from the iliac bone structures 17.

As shown generally in FIG. 1, pedicle screws are coupled to the rod 18 by set screws engaged with saddles, screw "tulips" and/or other connecting elements. Likewise, iliac connector 36 is engaged with the iliac screw 24, and is coupled to the rod 18, thereby connecting the iliac screw 24 to the rod 18. In some embodiments, the connector 36 is coupled to the rod 18 via a second fastener 54 (which may include, but is not limited to, a set screw). As described herein, the rod 18 may be coupled to a rod-receiver element 50 of the iliac connector 36 for selectively adjusting the direction of extension of at least a portion of a rod 18 in a first coronal plane (see generally, FIG. 2). The rod-receiver element 50 may also be rotatable 360 degrees in predetermined angular increments in place relative to components of the iliac connector 36 to adjust and/or fix the direction of extension of the at least a portion of the rod 18 in a first coronal plane such that the connector 36 is more easily engageable with iliac screws 24 and portions of rods 18 extending at a variety of non-orthogonal angles relative to each other.

Figure 2:
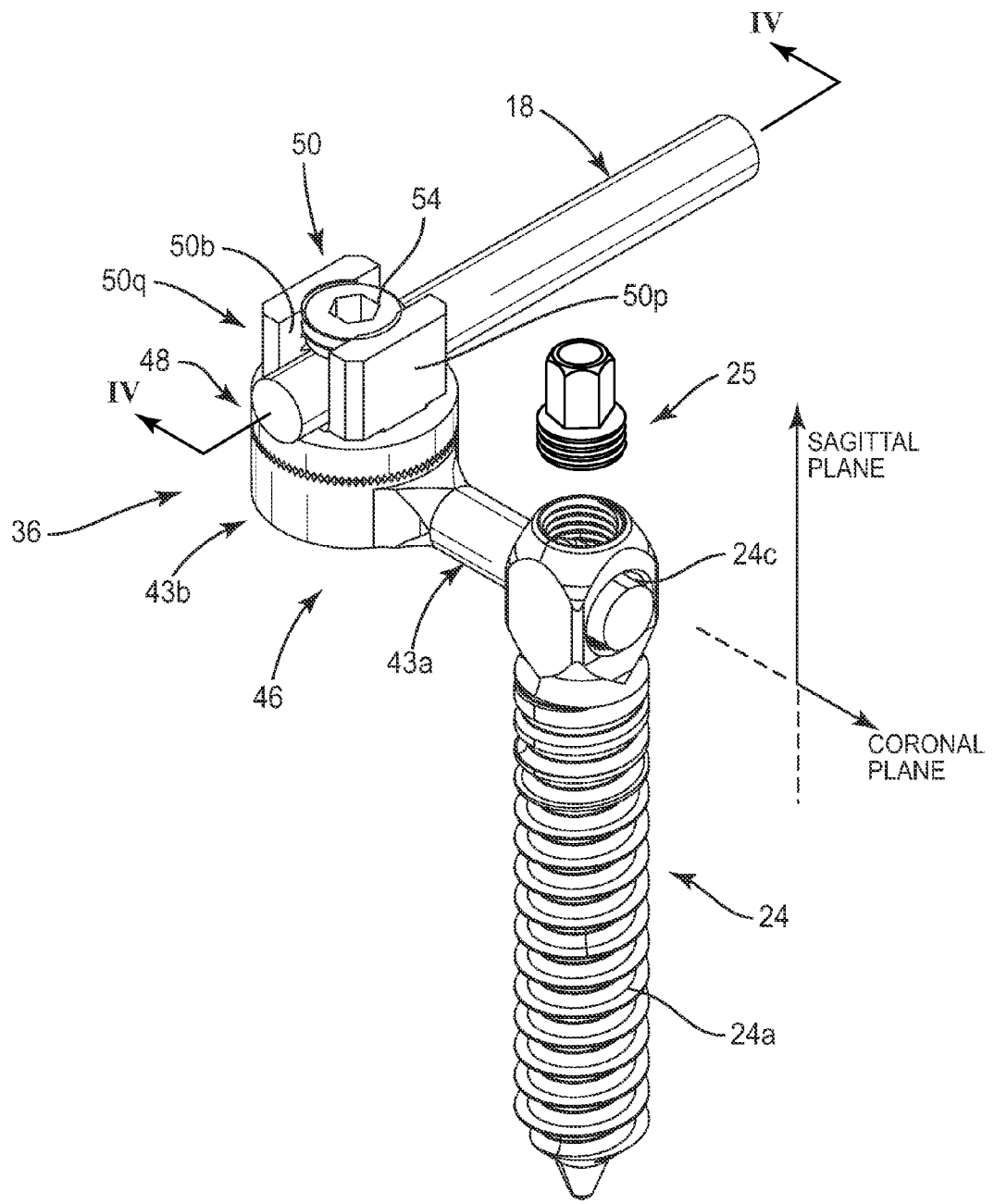
FIG. 2 is an unexploded perspective view of a connector/screw assembly according to an embodiment described herein and shown in FIG. 1.
Figure 3:
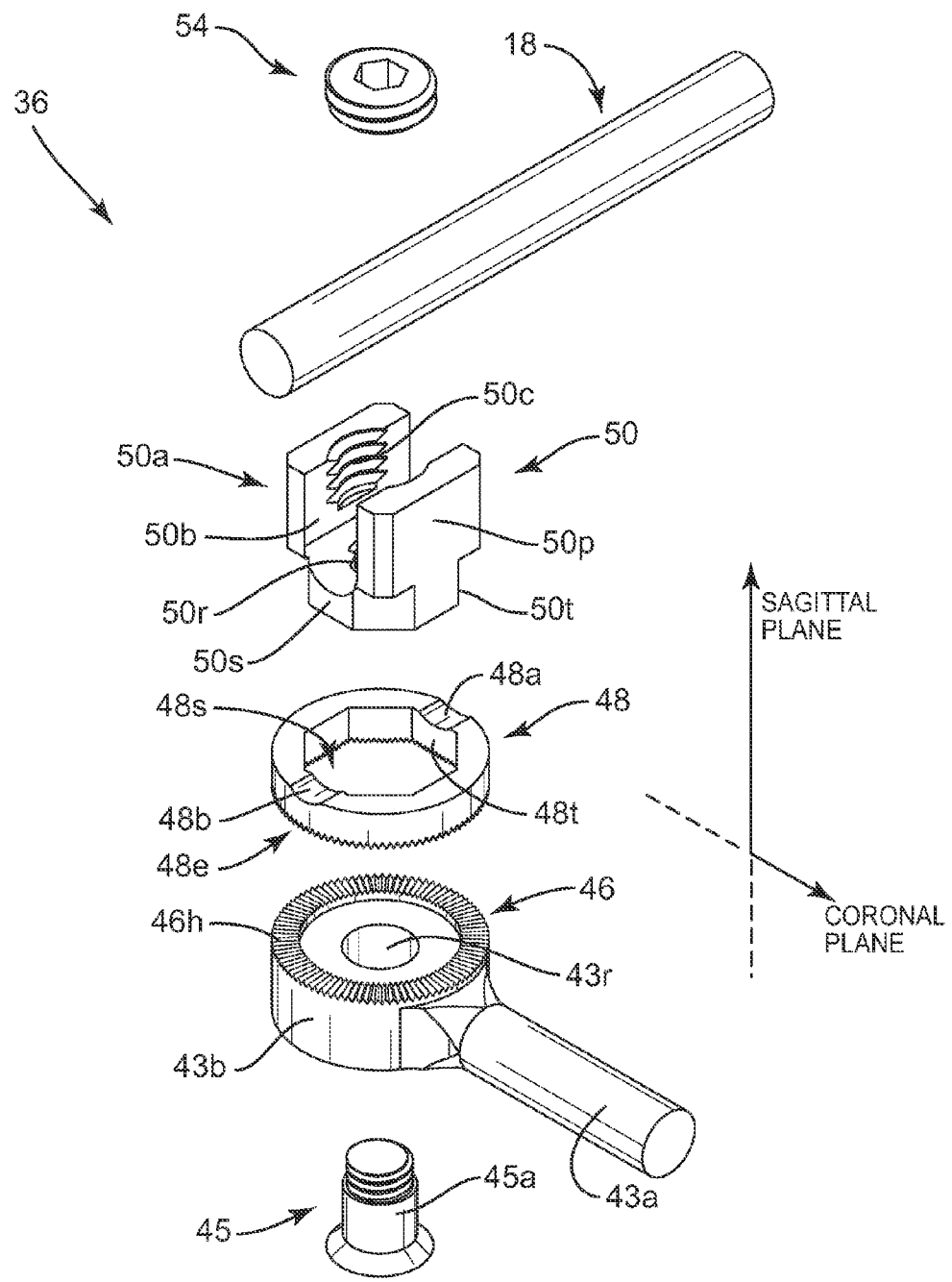
FIG. 3 is an exploded perspective view of the connector of FIG. 2.
Figure 4:
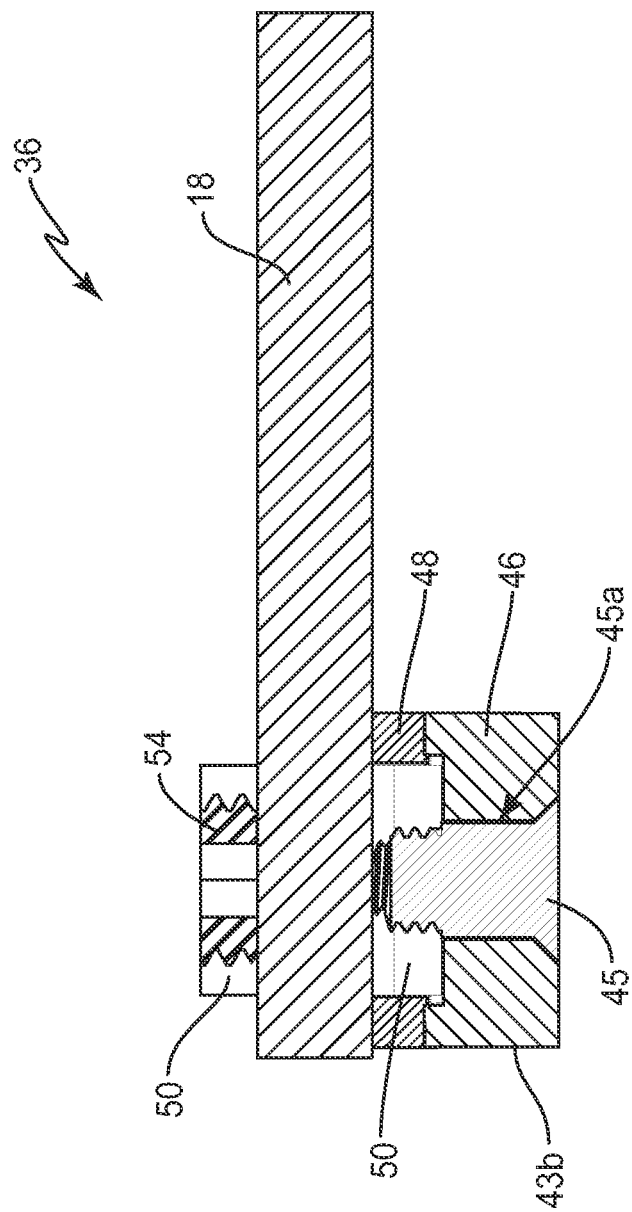
FIG. 4 is a sectional view of the connector of FIG. 2 taken along line IV-IV.

Referring to FIGS. 2 through 4, the connector 36 includes an extension element 46 adapted to be coupled to an iliac bone structure 17 (see FIG. 1) and a rod-receiver element 50 coupled to the extension element 46 for selectively adjusting the direction of extension of at least a portion of a rod 18 in a first coronal plane. Selective adjustment of the rod-receiver element 50 allows at least a portion of the rod 18 to engage the rod-receiver element 50 when the rod 18 extends within the vicinity of the spinal system 10 and the iliac bone structure 17.

Figure 5:
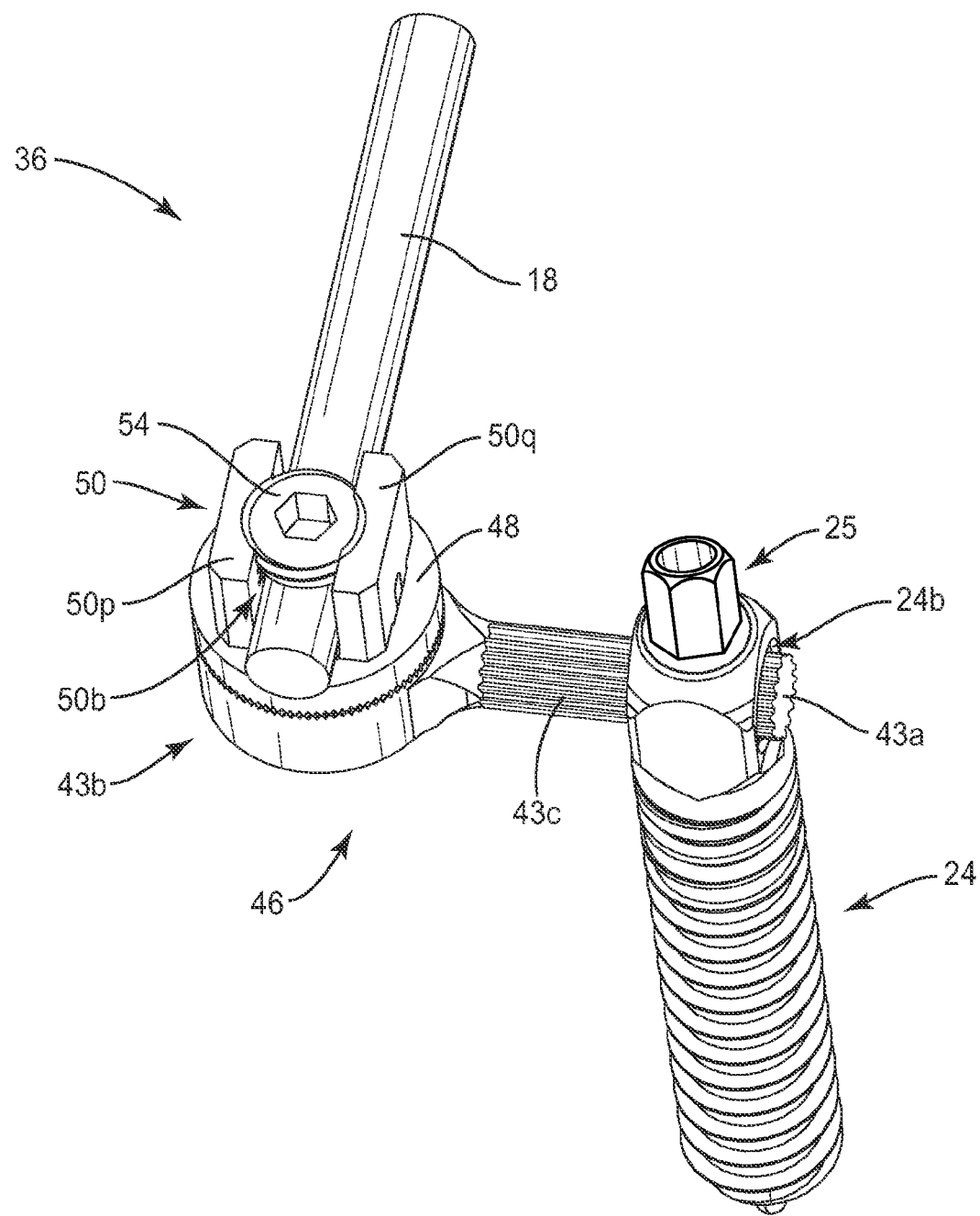
FIG. 5 is an unexploded perspective view of a connector/screw assembly according to another embodiment described herein.

As noted in FIG. 3, the rod-receiver element 50 defines a channel 50b having an open top such that at least a portion of the rod 18 may be inserted into the channel 50b by moving the rod 18 in a first sagittal plane. Furthermore, the rod-receiver element 50 is rotatable 360 degrees in predetermined angular increments in place relative to the extension element 46 to adjust and fix the direction of extension of the at least a portion of the rod 18 in the first coronal plane. In some embodiments (as shown, for example, in FIGS. 2, 3 and 5) the extension element 46 may comprise a rod portion 43a adapted to extend through a bore 24c defined in a fastener (such as an iliac screw 24). Furthermore, as shown in FIG. 5, the rod portion 43a may also define a splined surface comprising a plurality of ridges 43c extending along a longitudinal axis of the rod portion 43a. Furthermore, the plurality of ridges 43c may be adapted to be engaged with a complementary plurality of ridges 24b defined in the bore 24c of the iliac screw 24, such that the extension element 46 may be engaged with the iliac screw at a selected one of a predetermined range of angles relative to the first coronal plane.

Figure 9:
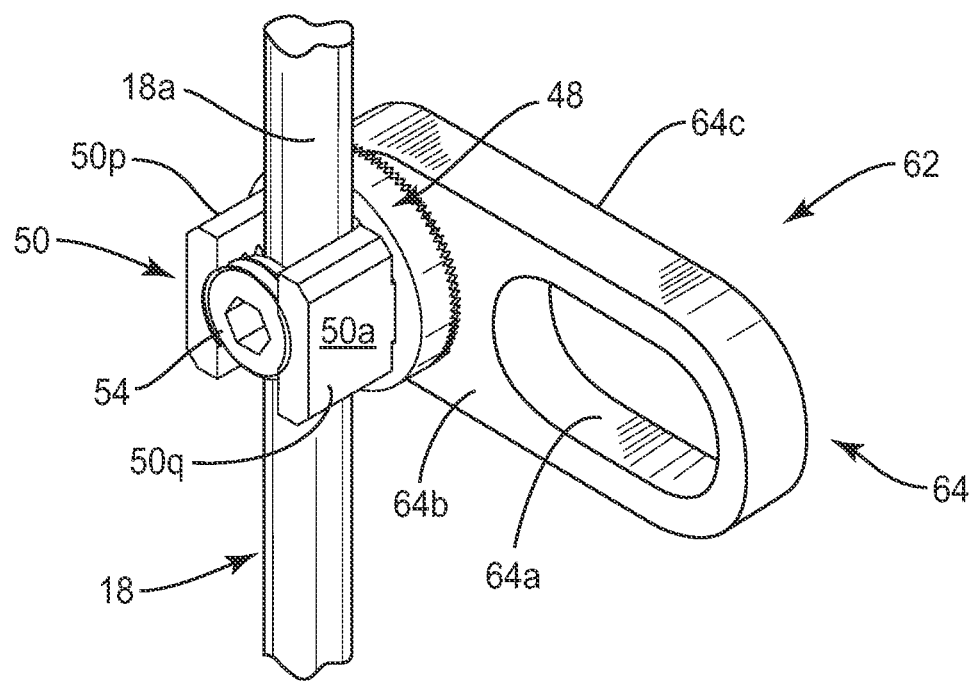
FIG. 9 is a perspective view of a connector according to another embodiment described herein.

In other embodiments, (such as that described in further detail herein with respect to FIG. 9) the extension element 46 may also comprise a plate member 64 defining a through-opening such as a slot 64a formed in an end portion of the plate member. In such embodiments, the slot 64a serves as an opening wherein a fastener (such as an iliac screw having a threaded post portion (not shown) is adapted to extend through the slot 64a to engage a bone structure (such as the iliac bone structure 17, shown in FIG. 1). The posted screw may be secured relative to the slot 64a by a nut and/or washer assembly. As shown in FIG. 9, slot 64a may be elongated so as to permit the end portion (and the entire plate member 64) to translate in a second coronal plane relative to the bone structure and the fastener extending through the slot 64a.

Referring to FIG. 3, in some embodiments the rod-receiver element 50 comprises a substantially U-shaped receptacle (see channel 50b defined in the rod-receiver element 50) having the open top for receiving a portion of the rod 18 as the rod 18 is moved in the first sagittal plane. In such embodiments, the U-shaped receptacle of the rod receiver element 50 comprises a pair of arms 50p, 50q defining the channel 50b such that at least a portion of the rod may be lowered and/or reduced into the open-top channel 50b in a direction substantially parallel to the sagittal plane. Furthermore, in some such embodiments, each of the pair of arms 50p, 50q comprises an inner threaded portion 50c, and the connector 36 apparatus further comprises a fastener (such as a set screw 54) configured to engage the inner threaded portions 50c so as to secure the at least a portion of the rod 18 in the channel 50b.

As shown in FIG. 3, the extension element 46 may further comprise a ring portion 43b defining a first aperture 43r (see also, element 46e, shown in FIGS. 6-8) extending therethrough. In such embodiments, the rod receiver element 50 may comprise a bearing surface defining a second aperture 50r. As shown in the cross-sectional view of FIG. 4, such embodiments may further comprise a first fastener 45 configured to be insertable through the complementary apertures 43r, 50r defined in the ring portion 43b and the rod receiver element, respectively, for coupling the extension element 46 to the rod-receiver element 50. In some such embodiments, the first fastener 45 may comprise a screw 45 threadably engaged with the first 43r and second 50r apertures defined in the ring portion 43b and the rod receiver element 50 for coupling the extension element 46 to the rod-receiver element 50. In some such embodiments, as shown generally in FIGS. 3 and 4, the first fastener 45 may comprise a screw 45 defining a screw shoulder 45a adjacent to a thread pattern defined on an outer surface of the screw 45 so as to rotatably couple the extension element 46 to the rod receiver element 50 when the screw 45 is secured to the extension element 46 and the rod-receiver element 50. The screw shoulder 45a may therefore allow the rod receiver to be slidably movable in a sagittal plane through a predetermined distance defined by a height of the screw shoulder 45a, thereby allowing for play in the connection between the extension element 46 and the rod receiver element 50 such that even when the first fastener (such as the screw 45, for example) is fully engaged to couple coupling the extension element 46 to the rod-receiver element 50, the rod-receiver element 50 may also be rotatable 360 degrees in place relative to extension element 46 and about the screw 45.

Referring again to FIGS. 2-5, the connector 36 may further comprise a washer 48 disposed between the rod-receiver element 50 and the ring portion 43b of the extension element 46, wherein at least a portion of the rod 18 engages the washer 48 when the rod 18 is inserted into the channel 50b defined in the rod-receiver element 50. For example, in some embodiments (such as that shown in the exploded view of FIG. 3), the washer 48 may comprise a pair of opposing generally V-shaped cut-outs 48a and 48b (see also FIG. 6) shaped to receive the rod 18 such that the rod 18 bears against the washer 48 so as to engage the washer 48 with the ring portion 43b of the extension element when the rod 18 is inserted into the channel 50b by moving the rod 18 generally in the sagittal plane (see, for example, the assembled perspective view of the connector shown in FIG. 2).

In some such embodiments, the portion of the rod 18 may be contained within the channel 50b and/or urged into contact with the washer 48 by a second fastener 54 (such as a set screw 54) threadably engaged with the rod-receiver element 50. The second fastener 54 may thus prevent relative movement between the portion of the rod 18 and the rod-receiver element 50 and may also serve to retain the portion of the rod 18 in the pair of opposing generally V-shaped cut-outs 48a and 48b (see also FIG. 6) defined in the washer 48. Referring to FIG. 3, the second fastener 54 may be threadably engaged with opposing inner surfaces 50c of the channel 50b. As shown in the exploded view of FIG. 3, the opposing inner surfaces 50c of the channel 50b may define threaded surfaces such that the second fastener 54 may contact the rod 18 as the second fastener 54 is tightened so that the rod 18 bears against the washer 48. The resulting bearing force of the washer 48 may effectively lock the rotatable rod-receiver element 50 in a predetermined angular position relative to the extension element 46 so as to enable selective adjustment of the direction of extension of at least a portion of a rod 18 in a first coronal plane. Referring to FIG. 3, the rod-receiver element 50 and the washer 48 may be fixed in a non-rotatable position relative to one another by a pair of flats 50s, 50t defined on an outer surface of the rod-receiver element 50 that may be operably engaged with corresponding flats 48s, 48t defined on an inner surface of the washer 48. Therefore, in such embodiments, the washer 48 may rotatable with the rod receiver element 50 as a joined pair relative to the extension element 46.

Furthermore, a variety of different locking mechanisms may be employed to allow the rod-receiver element 50 to be rotatable 360 degrees in predetermined angular increments in place relative to the extension element 46 so as to adjust and fix the direction of extension of the at least a portion of the rod 18 in the first coronal plane. For example, as shown in FIGS. 3 and 5, a first plurality of teeth 48e may be formed in the washer 48 and be adapted to mesh with a second plurality of teeth 46h formed in the ring portion 43b to lock the direction of extension of the at least a portion of the rod 18 in the first coronal plane. In such embodiments, a spacing between each pair of adjacent teeth in the first plurality of teeth 48e may define each corresponding predetermined angular increment of adjustment. For example, the peak-to-peak or valley-to-valley spacing between each pair of adjacent teeth in the pluralities of teeth 48e and 46h may be 6 degrees. Thus, the direction of extension of the channel 50b may be selectively adjusted and locked in 6-degree angular increments.

As noted herein, the rod 18 may be urged into contact with the washer 48 (and, in some embodiments, be urged into position in the pair of opposing generally V-shaped cut-outs 48a and 48b defined in the washer 48) by the second fastener 54. The tightening of the second fastener 54 may also urge the first plurality of teeth 48e (formed in the washer 48) towards the second plurality of teeth 46h formed in the ring portion 43b to lock the direction of extension of the at least a portion of the rod 18 in the first coronal plane.

To place the connector 36 is in its assembled condition, as shown in FIGS. 4 and 5, the rod-receiver element 50 is inserted through the washer 48 until the pair of flats 50s, 50t defined on an outer surface of the rod-receiver element 50 are operably engaged with corresponding flats 48s, 48t, respectively, defined on an inner surface of the washer 48. Before, during or after the engagement between the rod-receiver element 50 and the washer 48, it is understood that an adhesive such as, for example, a silicone adhesive may be applied to portions of the housing member 50 and/or to portions of the washer 48 to provide a more generally permanent engagement between the housing member 50 and the washer 48. For example, a silicone adhesive may be applied to the surfaces of the washer 48 defined by the flats 48s, 48t.

Referring generally to FIG. 3, the rod receiver element 50 (now coupled with the washer 48) is then moved adjacent to the ring portion 43b of the extension element 46. A first fastener 45 is then inserted through the complementary apertures defined in the ring portion 43b and the rod receiver element 50 for coupling the extension element 46 to the rod-receiver element 50. as described herein, the first fastener may comprise a screw 45 threadably engaged with the first and second apertures defined in the ring portion 43b and the rod receiver element 50 for coupling the extension element 46 to the rod-receiver element 50. In some such embodiments, as shown generally in FIGS. 3 and 4, the first fastener 45 may comprise a screw 45 defining a screw shoulder 45a adjacent to a thread pattern defined on an outer surface of the screw 45 so as to rotatably couple the extension element 46 to the rod receiver element 50 when the screw 45 is secured to the extension element 46 and the rod-receiver element 50. The screw shoulder 45a may therefore allow the rod receiver to be slidably movable in a sagittal plane through a predetermined distance defined by a height of the screw shoulder 45a, thereby allowing for play in the connection between the extension element 46 and the rod receiver element 50 such that even when the first fastener (such as the screw 45, for example) is fully engaged to couple coupling the extension element 46 to the rod-receiver element 50, the rod-receiver element 50 (and the washer 48, coupled thereto) may also be rotatable 360 degrees in place about the screw 45 and relative to the ring portion 43b of the extension element 46. As the rod-receiver element 50 and the washer 48 rotate, the direction of extension of the channel 50b is selectively adjusted. Since the center axis of the apertures, 43r, 50r, and therefore the substantially coaxial imaginary axis about which the rod-receiver element 50 and the washer 48 rotate, is perpendicular to a planar surface of the ring portion 43b, it is understood that the direction of extension of the channel 50b is selectively adjusted in a plane that is either substantially coplanar or parallel with the planar surface of the ring portion 43b (and at least substantially coplanar with the first coronal plane).

To lock the direction of extension of the channel 50b at a desired position, the housing member 50 and the washer 48 may be rotated to adjust the direction of extension of the channel 50b to the desired position, and the washer 48 may be moved towards the extension element 46 so that the plurality of teeth 48e of the washer 48 meshes with the plurality of teeth 46h of the ring portion 43b of the extension element 46. The meshing of the pluralities of teeth 48e and 46h prevents further rotation of the washer 48 relative to the extension element 46 and, correspondingly, the direction of extension of the channel 50b is locked.

It is understood that the direction of extension of the channel 50b may be selectively adjusted and locked in predetermined angular increments, with each predetermined angular increment corresponding to the spacing between each pair of adjacent teeth in the pluralities of teeth 48e and 46h. For example, the peak-to-peak or valley-to-valley spacing between each pair of adjacent teeth in the pluralities of teeth 48e and 46h may be 6 degrees. Thus, the direction of extension of the channel 50b may be selectively adjusted and locked in 6-degree angular increments.

After selectively adjusting the direction of extension of the channel 50b, and also locking the direction of extension of the channel 50b if desired, the rod 18 is inserted into the channel 50b by moving the rod 18 in a first sagittal plane (which, as described herein, may include a plane substantially perpendicular to the first coronal plane and/or substantially perpendicular to the planar surface of the ring portion 43b defining the plurality of teeth 46h). Once moved into the channel 50b at least a portion of the rod 18 engages the washer 48 and is seated in the cut-outs 48a and 48b. The set screw 54 is threadably engaged with the threaded inner surface 50c of arms 50p and 50q defining the channel 50b so that the set screw 54 extends into the channel 50b, contacting the rod 18 as shown generally in the sectional view of FIG. 4. Further threaded engagement between the set screw 54 and the threaded inner surface 50c causes the rod 18 to bear against the surfaces of the washer 48 defined by the cut-outs 48a and 48b, thereby substantially preventing relative movement between the rod 18 and the housing member 50.

Since the rod 18 is moved in a first sagittal plane and into the channel 50b so that at least a portion of the rod 18 engages the washer 48, it is understood that, by selectively adjusting the direction of extension of the channel 50b in the manner described herein, the direction of extension of the rod 18 is also selectively adjusted in a plane that is either substantially coplanar or parallel with one or more of the planar surfaces defining an upper surface of the ring portion 43b (such as, for example, the planar surface defining the plurality of teeth 46h). For the same reasons, it is further understood that, by selectively adjusting the direction of extension of the channel 50b in predetermined angular increments in the manner described above, the direction of extension of the rod 18 is also selectively adjusted in predetermined angular increments. And it is further understood that, by locking the direction of extension of the channel 50b in the manner described above, the direction of extension of the rod 18 is also locked.

FIGS. 9-13 depict alternative embodiments of the connector 36 wherein the extension element 46 comprises a plate member 64, 70, 78 defining respective apertures 64a, 70c, 78d suitable for attachment to a screw or other fastener having a post and/or threaded post top. FIGS. 6-13 also depict alternative embodiments wherein the rod-receiver element 50 is coupled to the extension element 46 in several different ways. It is understood that the various coupling techniques and structures depicted in FIGS. 9-13 for coupling the rod receiver element 50 with the extension element 46 (while shown and described in the context of a connector 36 having a plate member 64, 70, 78 serving as the extension element 46) may also be used in the embodiments shown in FIGS. 1-8 wherein the extension element 46 comprises a rod portion 43a and ring portion 43b. It is further understood that the various coupling techniques and structures depicted in FIGS. 1-8 for coupling the rod receiver element 50 with the extension element 46 (while shown and described in the context of an extension element 46 comprising a rod portion 43a and ring portion 43b) may also be used in the embodiments shown in FIGS. 9-13 wherein the extension element 46 includes a plate member 64, 70, 78 suitable for engagement with a fastener having a post and/or threaded post extending outward from a bony structure to which it may be attached.

Figure 6:
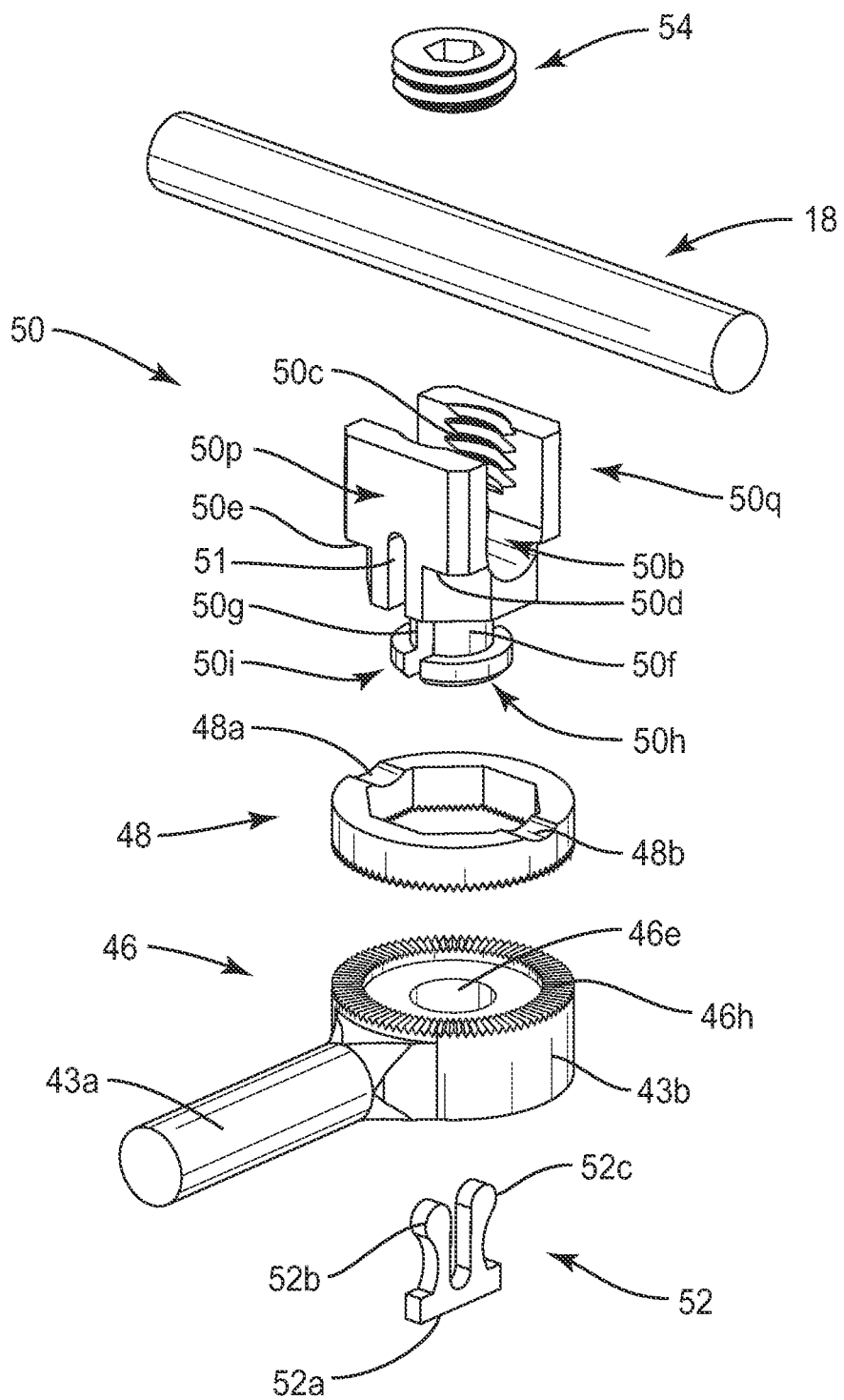
FIG. 6 is an exploded perspective view of a connector according to another embodiment described herein.
Figure 7:
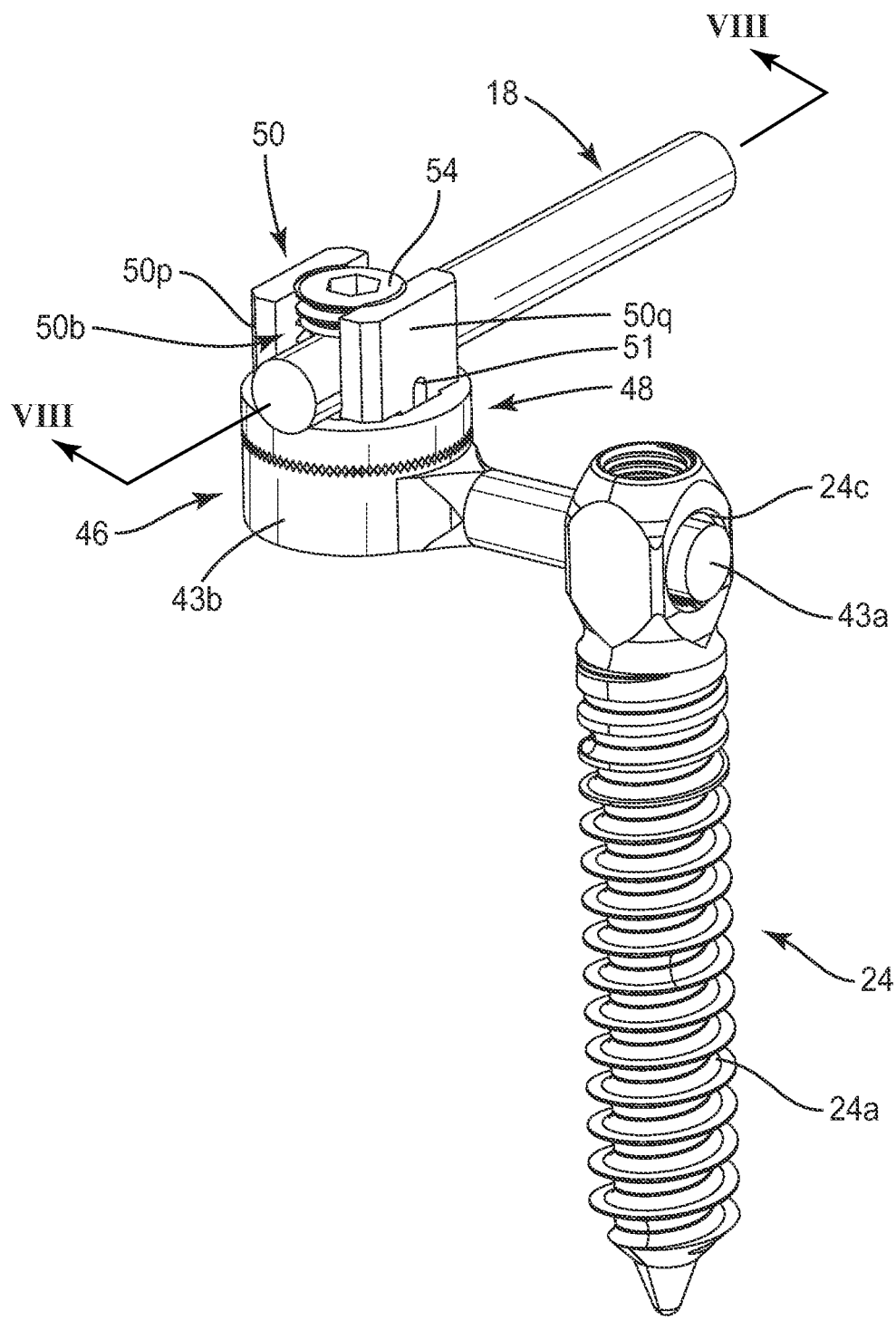
FIG. 7 is a perspective view of a connector according to another embodiment described herein.
Figure 8:
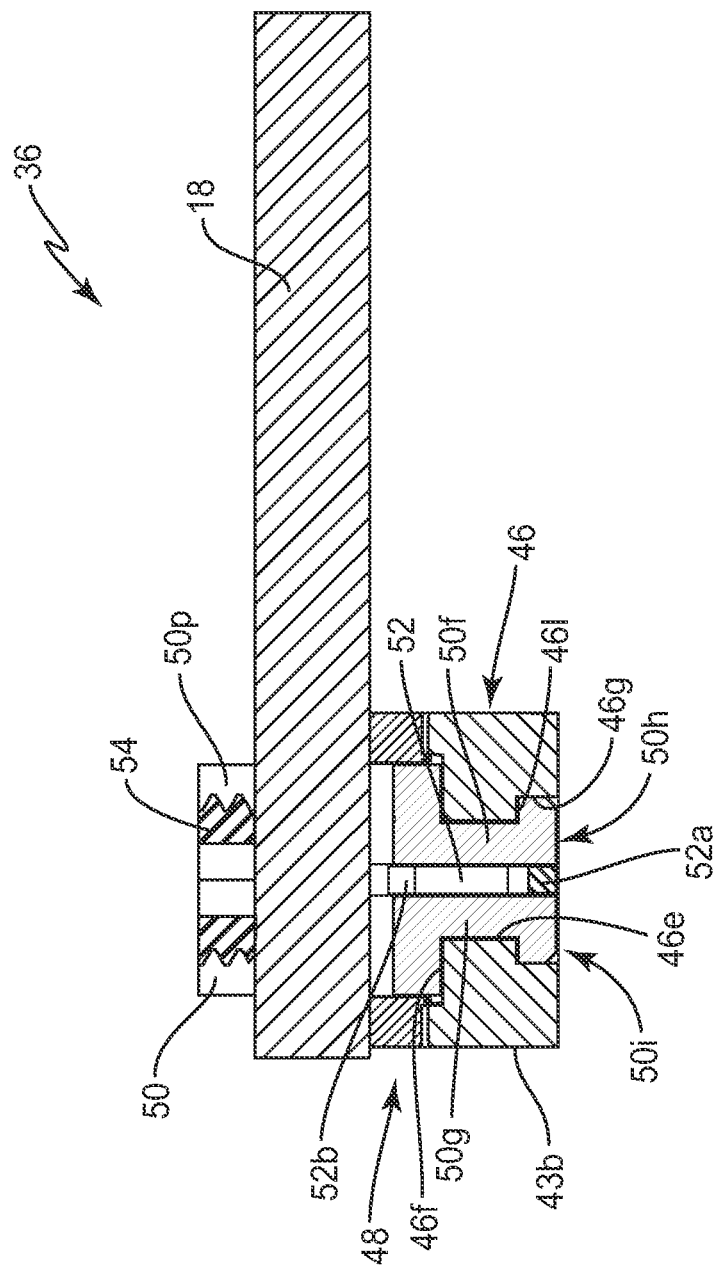
FIG. 8 is an unexploded sectional view of the connector of FIG. 7 taken along line VIII-VIII.

Referring to FIGS. 6 through 8, in some embodiments, the connector 36 includes a clip member 52 configured to couple the rod-receiver element 50 with the extension element 46. In some such embodiments, the extension element 46 includes a ring portion 43b defining a first aperture (such as a countersunk bore 46e). As shown in FIG. 8, the countersunk bore 46e is formed through the ring portion 43a, and includes a countersunk portion 46f and an increased-diameter portion 46g below the countersunk portion 46f. A plurality of teeth 46h is formed in a surface of the end portion 46a, with the plurality of teeth 46h partially circumferentially extending about the countersunk bore 46e. The increased-diameter portion 46g of the bore 46e defines a surface 46l (shown in FIG. 8).

In such embodiments, the rod-receiver element 50 comprises a pair of arms 50f, 50g extending from the rod-receiver element 50 and through the countersunk bore 46e to form a snap fit between the rod-receiver element 50 and the extension element 46. The arms 50f and 50g may include increased-size distal end portions 50h and 50i, respectively.

As shown in the exploded assembly FIG. 6, such embodiments may further comprise a clip member 52 that may also be inserted through the countersunk bore 46e from an underside of the ring portion 43b. As shown in FIG. 8, the clip member 52 may be disposed between the arms 50f, 50g of the rod-receiver element 50 to prevent the rod-receiver element 50 from decoupling from the extension element 46. For example, the clip member 52 may urge the distal end portions 50h, 50i of the arms 50f, 50g outward and into the increased-diameter portion 46g of the countersunk bore 46e such that the rod-receiver element 50 is firmly yet rotatably coupled to the ring portion 43b of the extension element 46.

A washer 48 includes a pair of opposing generally V-shaped cut-outs 48a and 48b. A plurality of teeth 48e is formed in a surface of the washer 48 opposing the cut-outs 48a and 48b.

As shown generally in FIG. 8, the clip member 52 may comprise a pair of legs 52b, 52c coupled by a connecting portion 52a. Each leg 52b, 52c may be configured to extend through the countersunk bore 46e so as to engage the ring portion 43b. Each leg 52b, 52c is also biased in a direction away from the other leg when the clip member 52 is disposed between the arms 50f, 50g of the rod-receiver element 50.

As described above with respect to FIGS. 2-5, the extension element 46 may further comprise a rod portion 43a adapted to extend through a bore 24b defined in a fastener (such as an iliac screw 24). Furthermore, as shown in FIG. 5, the rod portion 43a may also define a splined surface comprising a plurality of ridges 43c extending along a longitudinal axis of the rod portion 43a. Furthermore, the plurality of ridges 43c may be adapted to be engaged with a complementary plurality of ridges or splines 24b defined in the bore 24c of the iliac screw 24, such that the extension element 46 may be engaged with the iliac screw 24 at a selected one of a predetermined range of angles relative to the first coronal plane.

To place the connector 36 is in its assembled condition, as shown in FIGS. 7 and 8, the connector arms 50f and 50g of the rod-receiver element 50 are inserted through the washer 48 until the surfaces of the rod-receiver element 50 defined by the undercuts 50d and 50e engage the upper surfaces of the washer 48. Before, during or after the engagement between the rod-receiver element 50 and the washer 48, it is understood that an adhesive such as, for example, a silicone adhesive may be applied to portions of the rod-receiver element 50 and/or to portions of the washer 48 to provide a more generally permanent engagement between the rod-receiver element 50 and the washer 48. For example, a silicone adhesive may be applied to the surfaces of the upper surfaces of the washer 48 and/or surfaces of the rod-receiver element defined by undercuts 50d, 50e.

Referring generally to FIG. 8, the connector arms 50f and 50g of the rod-receiver element 50 are then inserted into the bore 46e of the plate member 46. As the connector arms 50f and 50g are inserted into the bore 46e, the increased-size distal end portions 50h and 50i engage the countersunk portion 46f, thereby causing at least the distal end portions 50h and 50i of the connector arms 50f and 50g, respectively, to flex towards each other so that the connector arms 50f and 50g may be inserted through the bore 46e.

Upon entry into the increased-diameter portion 46g of the bore 46e, the distal end portions 50h and 50i move back to their initial positions relative to one another, thereby forming a snap fit and coupling the rod-receiver element 50 to the ring portion 43b of the extension element 46, with the washer 48 disposed therebetween. It is understood that the rod-receiver element 50 and the washer 48 may have a limited degree of freedom of translation in an up-and-down direction, relative to the ring portion 43b and as shown generally in FIG. 8.

Referring to FIGS. 6 and 8, the clip member 52 is inserted into the bore 46e, causing the legs 52b and 52c to flex towards each other. Insertion of the clip member 52 is continued until the connecting portion 52a is substantially flush with a lower planar surface of the plate member ring portion 43b as shown in FIG. 8. At this point, the legs 52b and 52c are disposed between the connector arms 50e and 50f of the rod-receiver element 50, and at least the distal ends of the legs 52b and 52c have flexed away from each other and are disposed in the countersunk portion 46f of the bore 46e, engaging an upper surface of the ring portion 43b defined by the countersunk portion 46f. Due to the opposing directions of extension of the legs 52b and 52c, the legs 52b and 52c are biased away from each other when disposed between the arms 50e and 50f and engaging the countersunk portion 46f, thereby securing the clip member 52 to the plate member 46.

As a result of the disposal of the legs 52b and 52c of the clip member 52 between the connector arms 50f and 50g of the rod-receiver element 50, the connector arms 50f and 50g are prevented from moving towards each other so as to prevent the increased-size distal portions 50h and 50i of the connector arms 50f and 50g, respectively, from backing out through the bore 46e. Thus, the clip member 52 retains the rod-receiver element 50 to the plate member 46, preventing any decoupling therebetween.

At this point, due in part to the limited degree of freedom of translation in the up-and-down direction as viewed in FIG. 8, the rod-receiver element 50 and the washer 48 are free to rotate in place, up to 360 degrees and relative to the ring portion 43b, about an imaginary axis that is substantially coaxial with the center axis of the bore 46e. As the rod-receiver element 50 and the washer 48 rotate, the direction of extension of the channel 50b is selectively adjusted. Since the center axis of the bore 46e, and therefore the substantially coaxial imaginary axis about which the rod-receiver element 50 and the washer 48 rotate, is perpendicular to the upper planar surface of the extension element 46 defining the plurality of teeth 46h, it is understood that the direction of extension of the channel 50b is selectively adjusted in a plane that is either substantially coplanar or parallel with the upper planar surface of the extension element 46 defining the plurality of teeth 46h.

To lock the direction of extension of the channel 50b at a desired position, the rod-receiver element 50 and the washer 48 may be rotated to adjust the direction of extension of the channel 50b to the desired position, and the washer 48 may be moved towards the plate member 46 so that the plurality of teeth 48e of the washer 48 meshes with the plurality of teeth 46h of the extension element 46. The meshing of the pluralities of teeth 48e and 46h prevents further rotation of the washer 48 relative to the extension element 46. Thus, the direction of extension of the channel 50b is locked.

It is understood that the direction of extension of the channel 50b may be selectively adjusted and locked in predetermined angular increments, with each predetermined angular increment corresponding to the spacing between each pair of adjacent teeth in the pluralities of teeth 48e and 46h. For example, the peak-to-peak or valley-to-valley spacing between each pair of adjacent teeth in the pluralities of teeth 48e and 46h may be 6 degrees. Thus, the direction of extension of the channel 50b may be selectively adjusted and locked in 6-degree angular increments.

After selectively adjusting the direction of extension of the channel 50b, and also locking the direction of extension of the channel 50b if desired, the rod 18 is moved downward in a first sagittal plane and into the channel 50b defined by the arms 50p, 50q the rod-receiver element 50 so that a portion 18a of the rod 18 engages the washer 48 and is seated in the cut-outs 48a and 48b. The set screw 54 is threadably engaged with the threaded surface 50c so that the set screw 54 extends into the through-opening channel 50b, contacting the rod portion 18a. Further threaded engagement between the set screw 54 and the threaded inner surface 50c causes the rod portion 18a to bear against the surfaces of the washer 48 defined by the cut-outs 48a and 48b, thereby substantially preventing relative movement between the rod 18 and rod-receiver element 50.

Since the rod 18 is moved downward in a first plane substantially perpendicular to the upper planar surfaces of the extension element 46 (such as a planar surface of the ring portion 43b defining the plurality of teeth 46h), and into the channel 50b so that the rod portion 18a engages the washer 48, it is understood that, by selectively adjusting the direction of extension of the channel 50b in the manner described above, the direction of extension of the rod portion 18a is also selectively adjusted in a plane that is either substantially coplanar or parallel with planar surface of the ring portion 43b defining the plurality of teeth 46h. For the same reasons, it is further understood that, by selectively adjusting the direction of extension of the channel 50b in predetermined angular increments in the manner described above, the direction of extension of the rod portion 18a is also selectively adjusted in predetermined angular increments. And it is further understood that, by locking the direction of extension of the channel 50b in the manner described above, the direction of extension of the rod portion 18a is also locked.

The opposing iliac connector 34 also shown in FIG. 1 is substantially identical to the connector 36 and therefore will not be described in detail. The placement of connector 34 in its assembled condition is substantially identical to the above-described placement of the connector 36 in its assembled condition and therefore this placement will not be described in detail.

The engagement between the rod 20 and the connector 34 is substantially identical to the above-described engagement of the rod 18 with the connector 36 and therefore this engagement will not be described in detail. It is understood, however, that the locked directions of extension of the portions of the rod 20 engaged with the connector 34 may differ from the locked direction of extension of the rod portion 18a engaged with the connector 36.

Referring back to FIG. 1 with continuing reference to FIGS. 2-4 and 6-8, the threaded portion 24a of the iliac screw 24 is threadably engaged with the iliac bone structure 17 so that the iliac screw 24 extends from the iliac bone structure 17 in a generally anterior-to-posterior direction away from the spinal system 10. However, it is understood that, depending on the anatomical differences of various patients, the position of the iliac bone structure 17 may necessitate that the iliac screw 24 extend from the iliac bone structure in a direction that is substantially non-orthogonal relative to either of the sagittal and coronal planes. Thus, the selectable adjustability of the connector 36 as described herein may significantly aid a clinician in reducing and/or otherwise moving the rod 18 into the channel 50b defined by the rod-receiver element 50 of the connector 36.

Referring now to FIG. 9, in some embodiments, the connector 36 includes a plate member 64 (see also the plate members 70, 78 shown in FIGS. 10-13) serving as at least a portion of the extension element 46, the plate member 64 defining planar surfaces 64b and 64c, respectively, and slot 64a configured for receiving a posted screw or other fastener portion, wherein the fastener is configured for insertion into a bone structure such as the iliac bone structure 17 shown in FIG. 1.

The placement of the connector 62 in its assembled condition (i.e. the coupling of the rod-receiver element 50 with the washer 48 and/or extension element 64) is substantially identical to the placement of the connector 36 in its assembled condition, and therefore the assembly of the connector 62 will not be described in detail. It is understood that the rod-receiver element 50 is coupled to the plate member 64, with the washer 48 disposed therebetween, in the same manner as the housing member 50 is coupled to the extension element 46 of the connector 36 in the embodiment of FIGS. 1-8.

The implementation, arrangement and operation of the connector 62 within the vicinity of the spinal system 10 is substantially identical to the implementation, arrangement and operation of the connector 36 described above in connection with the embodiment of FIGS. 6-8, except that the plate member 64 is utilized in place of the rod portion 43b so as to be compatible with screws having a posted and/or threaded upper portion.

Referring again to FIG. 9, after engagement of the rod-receiver element 50 with the rod 18 in the manner described herein with respect to FIGS. 2-8, the embodiments of the connector 62 comprising plate member 64, may be positioned so that a posted screw (not shown) extends through the slot 64a of the connector 62. As a result, the rod 18 extends within the vicinity of the spinal system 10 (see generally, FIG. 1). At this point, a washer and nut assembly may be positioned so that a threaded upper portion of a posted screw extends through the washer and threadably engages a nut positioned above an upper planar surface 64b of the plate member 64.

It is understood that the slot 64a of the connector 62 enables the connector 62 to translate in a coronal plane, relative to the screw 24 and the iliac bone structure 17 (see generally, FIG. 1). As used herein, it is understood that the term "coronal plane" includes any plane of section in the anatomical position that generally passes vertically through the human body and is generally perpendicular to both the median (or sagittal) plane and the horizontal (or axial or transverse) plane, generally dividing the human body into anterior and posterior sections, and further includes any plane of section in the anatomical position that generally passes vertically through the human body, is generally perpendicular to the horizontal (or axial or transverse) plane, and is generally angularly oriented from the median (or sagittal) plane at an angle of orientation ranging from greater than zero degrees up to and including ninety degrees.

After the connector 62 is positioned as desired and/or necessary, the washer and nut assembly may be further threadably engaged with an upper threaded portion of a screw 24 (see generally FIG. 1) and is thereby tightened so that the any relative translation and/or movement, between the connector 62 and a bone structure (such as the iliac bone structure 17 depicted in FIG. 1), is prevented and the planar surface 64c of the plate member 64 is engaged with the bone structure, thereby coupling the connector 62 to the bone structure. Each of the planar surfaces 64b, 64c of the plate member 64 of the connector 62 generally lies in a coronal plane within the vicinity of the spinal system 10. Since, as described above, the direction of extension of the rod portion 18a is able to be selectively adjusted in a plane that is either parallel or substantially coplanar with one or more of the planar surfaces 64b, 64c, it follows that the direction of extension of the rod portion 18a is able to be selectively adjusted in a coronal plane within the vicinity of the spinal system 10.

As further shown in FIG. 1, the rod-receiver element 50 of the connector 36 has been rotated, relative to the extension element 46, so that the rod 18 engaged with the rod-receiver element 50 of the connector 36 extends in a generally vertical direction in a coronal plane within the vicinity of the spinal system 10. Dissimilarly, the corresponding rod-receiver element 50 of the connector 34 has been rotated to the right. Thus, the portions of the rod 18 engaged with the connectors 34 and 36 extend in coronal planes within the vicinity of the spinal system 10, but in directions that vary from each other and the rods 18, 20.

Instead of engaging the rod 18 with the connectors 34, 36 and then coupling the connectors 34, 36 to the iliac bone structures 17 respectively, it is understood that any of the various connectors 34, 36, 62, 68, 76 described herein may first be coupled to the iliac bone structure 17, respectively, and the rod 18 may then be lowered and/or reduced in the first sagittal plane into the channel 50b of the connectors 34, 36, 62, 68, 76. It is further understood that, prior to moving the rod 18 in the first sagittal plane to engage the rod-receiving element 50, the directions of extension of the channels 50b of the connectors 34, 36, 62, 68, 76 may be locked as described herein with respect to the various locking mechanisms suitable for fixing the direction of extension of the at least a portion of the rod 18 in the first coronal plane.

It is understood that the directions of extension of different portions of the rod 18 in one or more coronal planes within the vicinity of the spinal system 10 may each be selectively adjusted to form a wide variety of arrangement for a wide variety of reasons such as, for example, in order to avoid and/or clear features of an iliac bone structure, 17, vertebrae 12, 14 and/or 16, and/or other natural and/or artificial structures connected to one or more of the vertebrae, extending between two or more of the vertebrae, and/or connected to the rod 18 and/or the connectors 34, 36, 62, 68, 76. It is further understood that the connectors 34, 36, 62, 68, 76 described herein may also be used to couple the rods 18, 20 to a variety of bone fasteners, including but not limited to iliac screws, pedicle screws, posted pedicle screws, multi-axial screws, fixed angle screws, and other fasteners.

It is understood that the implementation and arrangement of the rod 20, and the connector 34 engaged therewith, within the vicinity of the spinal system 10 is substantially identical to the above-described implementation and arrangement of the rod 18, and the connector 36 engaged therewith, and therefore will not be described in detail.

In operation, the rods 18 and 20, and the connectors 34, 36 assist in providing immobilization and/or stabilization to the spinal system 10 by anchoring a portion of the rods 18, 20 with an iliac bone structure 17 such that the spinal system 10 (which may include, but is not limited to a system of bone fasteners, cross slinks, and other spinal instrumentation) is coupled to at least a portion of an iliac bone at a fixation point (such as an iliac bone structure 17).

It is further understood that the rods 18 and 20, and the connectors 34, 36 may also assist in providing immobilization and/or stabilization to the spinal system 10 via attachment directly to pedicle screws, and/or may serve as an adjunct to fusion of one or more portions of the spinal system 10. It is understood that the extent of displacement between the vertebrae 12 and 14, and/or the vertebrae 14 and 16, and/or other vertebrae in the spinal column of the spinal system 10 may be reduced, and/or one or more pairs of adjacent vertebrae may be maintained in a desired spatial relationship.

Figure 10:
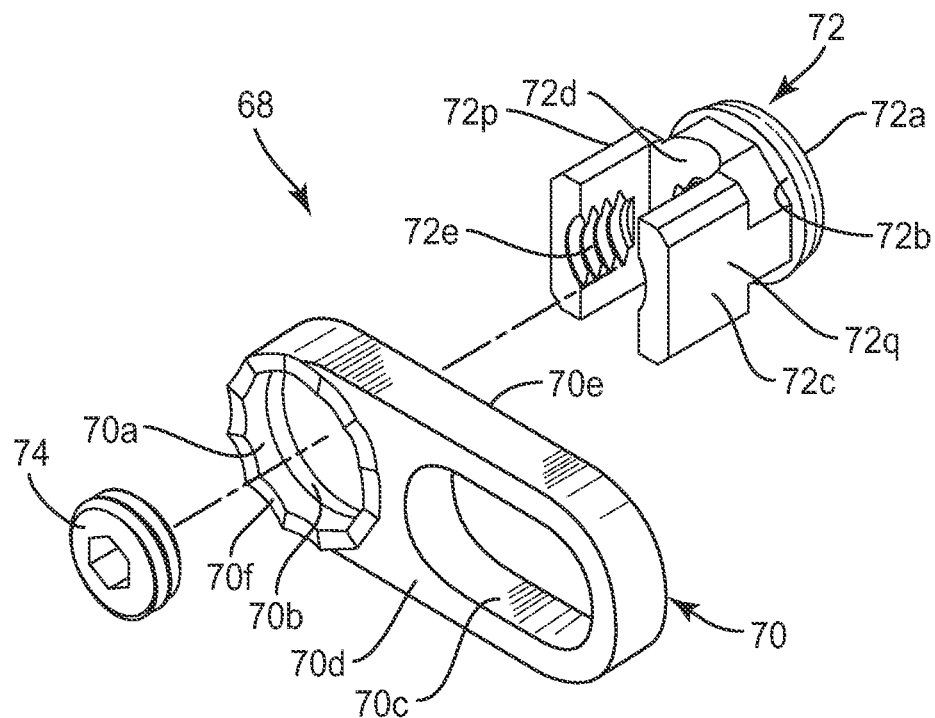
FIG. 10 is an exploded perspective view of a connector according to another embodiment described herein.
Figure 11:
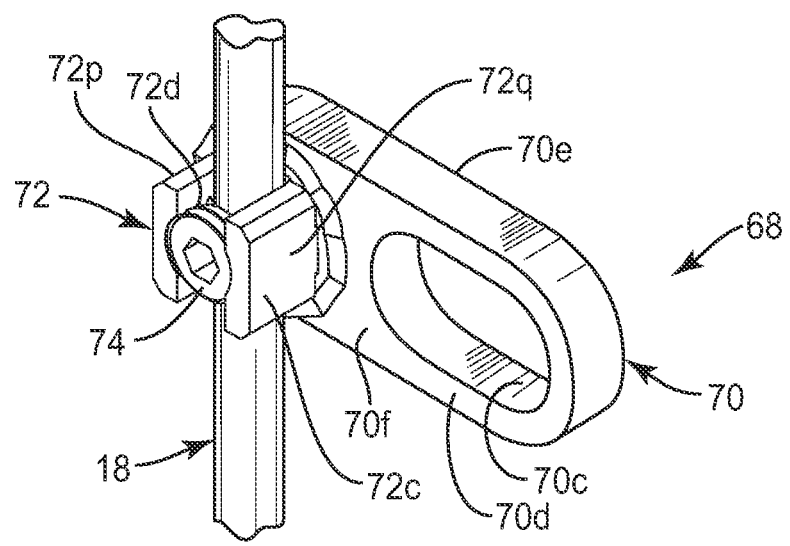
FIG. 11 is an unexploded perspective view of the connector assembly of FIG. 10.

Referring to FIGS. 10 and 11, another embodiment of a connector is generally referred to by the reference numeral 68. As is the case with the embodiment shown in FIG. 9, connector 68 includes a plate member 70 serving as the extension element. The plate member 70 includes a bore 70a defining a tapered surface 70b and an opening such as a slot 70c formed therethrough. The plate member 70 defines a planar surface 70d and a planar surface 70e, the edge of which is shown in FIG. 10. A plurality of partially-circumferentially-extending grooves 70f is formed in the planar surface 70d of the plate member 70, with each groove in the plurality of grooves 70f being adjacent the bore 70a and diametrically opposing one other groove in the plurality of grooves 70f.

A column 72 includes a head portion 72a defining a shoulder 72b, and a cylindrical portion 72c extending from the head portion 72a. A channel 72d is defined in the cylindrical portion 72c. A threaded inner surface 72e is defined on inner surfaces of arms 72p, 72q forming the through-opening 72d. The connector 68 further includes a fastener such as a set screw 74.

To place the connector 68 in its assembled condition, as shown in FIG. 11, the cylindrical portion 72c of the column 72 is inserted into the bore 70a of the plate member 70, until the shoulder 72b contacts the tapered surface 70b of the bore 70a. At this point, the column 72 is free to rotate in place, up to 360 degrees and relative to the plate member 70, about an imaginary axis that is substantially coaxial with the center axis of the bore 70a. As the column 72 rotates, the direction of extension of the channel 72d is selectively adjusted. Since the center axis of the bore 70a, and therefore the substantially coaxial imaginary axis about which the column 72 rotates, is perpendicular to the planar surfaces 70d and 70e, it is understood that the direction of extension of the channel 72d is selectively adjusted in a plane that is either substantially coplanar or parallel with the planar surfaces 70d and/or 70e.

After selectively adjusting the direction of extension of the channel 72d, the rod 18 is moved downward (i.e. in a first sagittal plane) into the channel 72d so that the rod portion 18a is seated between the arms 72p, 72q of the column 72, and in the pair of opposing grooves in the plurality of grooves 70f that corresponds to the direction of extension of the channel 72d. Thus, it is understood that by rotating the column 72 to selectively adjust the direction of extension of the channel 72d, the direction of extension of the rod portion 18a is also selectively adjusted in a plane that is either substantially coplanar or parallel with the planar surfaces 70d and/or 70e.

The set screw 74 is threadably engaged with the inner threaded surfaces 72e of the arms 7p, 72q so that the set screw 74 extends into the channel 72d, contacting the rod portion 18a. Further threaded engagement between the set screw 74 and the inner threaded surface 72e cause the rod portion 18a to bear against the pair of opposing grooves in the plurality of grooves 70f, thereby substantially preventing relative movement between the rod 18 and the column 72.

It is understood that the seating of the rod portion 18a in the pair of opposing grooves in the plurality of grooves 70f locks the direction of extension of the rod portion 18a. It is further understood that the direction of extension of the rod portion 18a may be selectively adjusted and locked in predetermined angular increments, with each predetermined angular increment corresponding to the spacing between adjacent grooves in the plurality of grooves 70f. For example, the center-to-center spacing between adjacent grooves in the plurality of grooves 70f may be 30 degrees. Thus, the direction of extension of the rod portion 18a may be selectively adjusted in 30-degree angular increments.

The implementation, arrangement and operation of the connector 68 within the vicinity of the spinal system 10 is substantially identical to the implementation, arrangement and operation of the connector 36 described above in connection with the embodiments of FIGS. 1-8, and therefore will not be described in detail. It is understood that a bone fastener (including, but not limited to an iliac screw 24 having a posted and/or threaded upper portion) extends through the slot 70c, and that the planar surface 70e engages a bone structure (such as the iliac bone structure 17, shown generally in FIG. 1). It is further understood that each of the planar surfaces 70d and 70e lies in a coronal plane within the vicinity of the spinal system 10.

Figure 12:
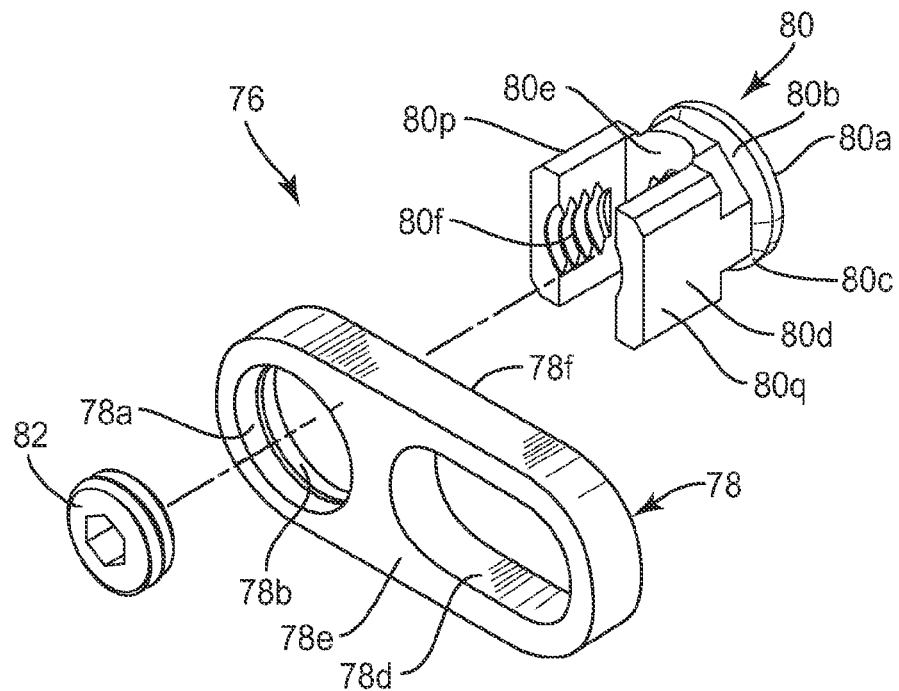
FIG. 12 is a perspective view of a connector according to another embodiment described herein.
Figure 13:
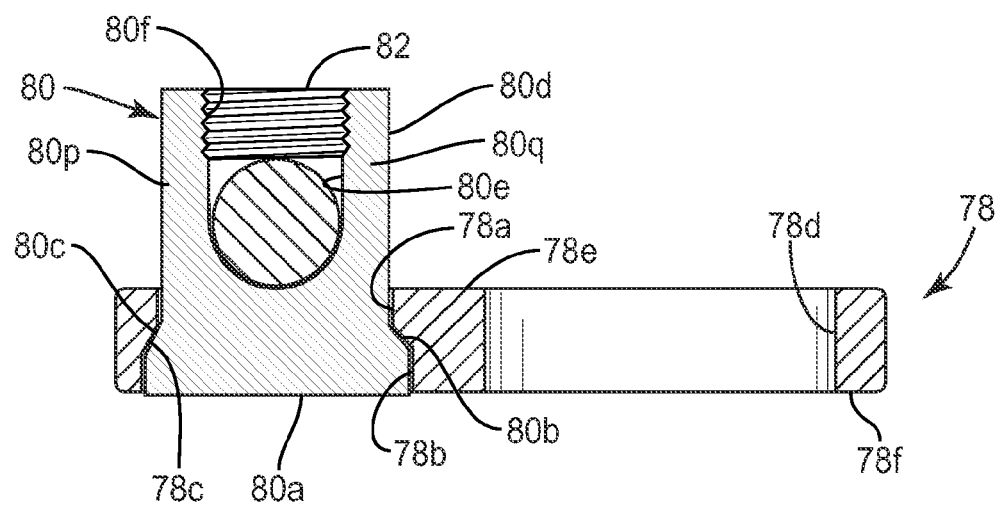
FIG. 13 is an unexploded sectional view of the connector of FIG. 12.

Referring to FIGS. 12 and 13, another embodiment of a connector is generally referred to by the reference numeral 76. A plate member 78 includes a bore 78a having an increased-diameter portion 78b and defining a tapered internal surface 78c. An opening such as a slot 78d is formed through the plate member 78. The plate member 78 defines a planar surface 78e and a planar surface 78f, the edge of which is shown in FIGS. 9 and 10.

A column 80 includes a head portion 80a defining a shoulder 80b which, in turn, defines a tapered external surface 80c. A cylindrical portion 80d extends from the head portion 80a, and a channel 80e is defined in the cylindrical portion 80d, forming a pair of opposing arms 80p, 80q. An inner threaded surface 80f is defined in the arms 80p, 80q into the channel 80e. The connector 76 further includes a fastener such as a set screw 82 configured to be threadably engaged with the inner threaded surface 80f.

To place the connector 76 in its assembled condition, as shown in FIG. 13, the cylindrical portion 80d of the column 80 is inserted into the bore 78a of the plate member 78 until the tapered external surface 80c of the column 80 mates with the tapered internal surface 78c defined by the bore 78a of the plate member 78. At this point, the column 80 is free to rotate in place, up to 360 degrees and relative to the plate member 78, about an imaginary axis that is substantially coaxial with the center axis of the bore 78a. As the column 80 rotates, the direction of extension of the channel 80e is selectively adjusted. Since the center axis of the bore 78a, and therefore the substantially coaxial imaginary axis about which the column 80 rotates, is perpendicular to the planar surfaces 78e and 78f, it is understood that the direction of extension of the channel 80e is selectively adjusted in a plane that is either substantially coplanar or parallel with the planar surfaces 78e and/or 78f.

After selectively adjusting the direction of extension of the channel 80e, the rod 18 is moved downward (i.e. in a first sagittal plane) into the channel 80e so that the rod portion 18a is seated between the arms 80p, 80q of the column 80, so that the rod portion 18a is engaged with the column 80. Thus, it is understood that by rotating the column 80 to selectively adjust the direction of extension of the channel 80e, the direction of extension of the rod portion 18a is also selectively adjusted in a plane that is either substantially coplanar or parallel with the planar surfaces 78e and 78f. It is further understood that column 80 may be rotated with the rod portion 18a engaged with the column 80 so that both of the directions of extension of the channel 80e and the rod portion 18a are selectively adjusted in a plane that is either substantially coplanar or parallel with the planar surfaces 78e and 78f.

The set screw 82 is threadably engaged with the inner threaded surfaces 80f of the opposing arms 80p, 80q so that the set screw 82 extends into the channel 80e, contacting the rod portion 18a. Further threaded engagement between the set screw 82 and the inner threaded surfaces 80f causes the rod portion 18a to bear against the planar surface 78e, thereby substantially preventing any relative movement between the rod 18 and the column 80.

Further threaded engagement between the set screw 82 and the inner threaded surfaces 80f draws the column 80 upward, as shown in FIG. 13, and causes the mating of the external surface 80c of the column 80 and the internal surface 78c of the plate member 78 to form a taper lock between the column 80 and the plate member 78, thereby preventing further rotation of the column 80 relative to the plate member 78. It is understood that the forming of the taper lock between the column 80 and the plate member 78 locks the direction of extension of the rod portion 18a. It is further understood that the direction of extension of the rod portion 18a may be selectively adjusted and locked in an infinite number of angular increments.

The implementation, arrangement and operation of the connector 76 within the vicinity of the spinal system 10 is substantially identical to the implementation, arrangement and operation of the connector 36 described above in connection with the embodiments of FIGS. 1-9, and therefore will not be described in detail. It is understood that a bone fastener (including, but not limited to an iliac screw 24), extends through the slot 78d, and that the planar surface 78f engages a bone structure (including, but not limited to an iliac bone structure 17 such as the prepared surface of the iliac crest shown generally in FIG. 1). It is understood that each of the planar surfaces 70e and 70f lies in a coronal plane within the vicinity of the spinal system 10.

An apparatus for stabilizing a spinal system has been described, comprising an extension element adapted to be coupled to an iliac bone structure and a rod-receiver element coupled to the extension element for selectively adjusting the direction of extension of at least a portion of a rod in a first coronal plane. At least a portion of the rod engages the rod-receiver element when the rod extends within the vicinity of the spinal system and the iliac bone structure. Specifically, in some embodiments, the rod-receiver element defines a channel having an open top such that at least a portion of the rod may be inserted into the channel by moving the rod in a first sagittal plane. Furthermore, the rod-receiver element may be rotatable 360 degrees in predetermined angular increments in place relative to the extension element to adjust and fix the direction of extension of the at least a portion of the rod in the first coronal plane.

A method of stabilizing a spinal system has been described. In one embodiment, the method comprises: engaging a fastener with an iliac bone structure; connecting the fastener to a rod extending within the vicinity of the spinal system by moving the rod in a first sagittal plane; and selectively adjusting the direction of extension of at least a portion of the rod in a first coronal plane in predetermined angular increments.

Another embodiment for stabilizing a spinal system has also been described, wherein the apparatus comprises an extension element adapted to be coupled to a bone structure, wherein the extension element comprises a rod portion adapted to extend through a bore defined in a bone fastener. Such embodiments further comprise a rod-receiver element coupled to the extension element for selectively adjusting the direction of extension of at least a portion of a rod in a first coronal plane. The rod-receiver element defines a channel having an open top such that at least a portion of the rod may be inserted into the channel by moving the rod in a first sagittal plane. The rod-receiver element is also rotatable 360 degrees in predetermined angular increments in place relative to the extension element to adjust and fix the direction of extension of the at least a portion of the rod in the first coronal plane, wherein the at least a portion of the rod engages the rod-receiver element when the rod extends within the vicinity of the spinal system and the bone structure.

It is understood that any foregoing spatial references, such as "upper," "lower," "above," "below," "between," "vertical," "angular," "up," "down," "right," "left," etc., are for the purpose of illustration only and do not limit the specific orientation or location of the structure described above.

Moreover, it is understood that any of the above-described connectors 34, 36, 62, 68 and/or 76 may be used in the iliac bones, in any iliac bone structure and/or in any location, and with any type of vertebra and/or any natural and/or artificial structure extending to or from the vertebra, within the spinal system 10. Further, it is understood that any of the above-described extension elements 46, 64, 70 and/or 78 may be rotated relative to any of the rods 18 and/or 20 engaged therewith, and/or relative to any iliac and/or pedicle screw 24 or other fastener engaged therewith. Still further, it is understood that conventional stabilizer components may be disposed in channels formed in one or more of the above-described plate members 46, 64, 70 and/or 78 so that any of the screws 24 or other fasteners (including but not limited to iliac and pedicle screws) engaged with any of the plate members 46, 64, 70 and/or 78 also extend through the stabilizer component. It is further understood that the cross-sections of the rods 18 and/or 20 extending within the vicinity of the spinal system 10 may be varied, and that the corresponding cross-sections of the channels 50b, 72d and/or 80e into which the rods 18 and/or 20 may be placed may also be correspondingly varied.

Also, it is understood that each of the above-described embodiments may be combined in whole or in part with one or more of the other above-described embodiments. It is further understood that each of the above-described embodiments may be combined in whole or in part with other components, devices, systems, methods and/or surgical techniques known to those skilled in the art to provide spinal stabilization.

Although exemplary embodiments of this invention have been described in detail above, those skilled in the art will readily appreciate that many other modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. An apparatus for stabilizing a spinal system, the apparatus comprising:
   an extension element adapted to be coupled to a bone structure, the extension element comprising a ring portion defining a first aperture, the ring portion comprising an upper surface including a plurality of teeth;
   a rod-receiver element comprising a pair of spaced apart arms extending through the first aperture, the rod-receiver element defining a channel having an open top such that at least a portion of the rod may be inserted into the channel by moving the rod in a first sagittal plane, the rod-receiver element being rotatable 360 degrees in predetermined angular increments in place relative to the extension element to adjust and fix the direction of extension of the at least a portion of the rod in a first coronal plane; and a clip member comprising a pair of legs coupled by a connecting portion, the clip member being disposed between the arms such that the connecting portion is flush with a bottom surface of the ring portion and the clip member is secured to the ring portion, wherein the at least a portion of the rod engages the rod-receiver element when the rod extends within the vicinity of the spinal system and the bone structure.

2. The apparatus of claim 1 wherein the extension element comprises a rod portion adapted to extend through a bore defined in a fastener.

3. The apparatus of claim 2 wherein the rod portion comprises a plurality of ridges extending along a longitudinal axis of the rod portion, the plurality of ridges adapted to be engaged with a complementary plurality of ridges defined in the bore.

4. The apparatus of claim 1 wherein the extension element comprises a plate member defining an opening and wherein a fastener is adapted to extend through the opening to engage the bone structure.

5. The apparatus of claim 1, wherein the rod-receiver element comprises a pair of second arms defining a substantially U-shaped receptacle defining the channel having the open top for receiving the at least a portion of the rod as the rod is moved in the first sagittal plane, wherein each of the pair of second arms comprises a threaded upper portion, the apparatus further comprising:

a set screw configured to engage the threaded upper portions so as to secure the at least a portion of the rod in the channel.

6. The apparatus of claim 1 wherein distal ends of the legs are disposed in a countersunk portion of the first aperture when the connecting portion is flush with the bottom surface.

7. The apparatus of claim 6 further comprising a washer disposed between the rod receiver element and the ring portion of the extension element wherein the at least a portion of the rod engages the washer when the at least a portion of the rod is inserted into the channel.

8. The apparatus of claim 7 further comprising a second fastener threadably engaged with the rod-receiver element for preventing relative movement between the at least a portion of the rod and the rod-receiver element, the second fastener configured to contact the at least a portion of the rod so that the at least a portion of the rod bears against the washer.

9. The apparatus of claim 7 wherein a first plurality of teeth is formed in the washer and is adapted to mesh with the teeth formed in the ring portion to lock the direction of extension of the at least a portion of the rod in the first coronal plane; and wherein a spacing between each pair of adjacent teeth in the first plurality of teeth defines each corresponding predetermined angular increment.

10. The apparatus of claim 6 wherein the first aperture comprises an increased-diameter portion below the countersunk portion, the arms having increased-size distal end portions that are disposed in the increased-diameter portion to form a snap fit and couple the rod-receiver element to the ring portion.

11. The apparatus of claim 10 wherein:
the first aperture comprises an increased diameter portion below the countersunk portion; and
distal ends of the legs engage the legs engage a surface of the ring that defines the countersunk portion.

12. The apparatus of claim 1 wherein the
form a snap fit between the rod-receiver element and the extension element; and wherein each of the pair of legs is biased in a direction away from the other leg when the clip member is disposed between the arms of the rod-receiver element.

13. The apparatus of claim 1 wherein the rod-receiver element comprises a column comprising:
a head portion defining a shoulder; and
a cylindrical portion extending from the head portion, the cylindrical portion defining the channel having the substantially open top such that at least a portion of the rod may be inserted into the channel by moving the rod in a first sagittal plane.

14. A method of stabilizing a spinal system, the method comprising:
engaging a fastener with an iliac bone structure;
connecting the fastener to a rod extending within the vicinity of the spinal system;
engaging a connecting apparatus with the fastener, the connecting apparatus comprising:
an extension element comprising a ring portion defining a first aperture, the ring portion comprising an upper surface including a plurality of teeth,
a rod-receiver element comprising a pair of spaced apart arms extending through the first aperture, the rod-receiver element defining a channel having an open top, the rod-receiver element being rotatable relative to the extension element, and
a clip member comprising a pair of legs coupled by a connecting portion, the clip member being disposed between the arms such that the connecting portion is flush with a bottom surface of the ring portion and the clip member is secured to the ring portion;
moving the rod in the first sagittal plane into the channel to couple the rod to the connecting apparatus;
selectively adjusting the direction of extension of at least a portion of the rod in a first coronal plane by adjusting the connecting apparatus in predetermined angular increments; and
locking the direction of extension of the at least a portion of the rod.

15. The method of claim 14
wherein the step of selectively adjusting the direction of extension of the at least a portion of the rod in the first coronal plane comprises rotating the rod-receiver element in place relative to the extension element.

16. An apparatus for stabilizing a spinal system, the apparatus comprising:
an extension element adapted to be coupled to a bone structure, wherein the extension element comprises a rod portion adapted to extend through a bore defined in a bone fastener, the extension element comprising a ring portion defining a first aperture, the ring portion comprising an upper surface including a plurality of teeth;
a rod-receiver element comprising a pair of spaced apart arms extending through the first aperture, the rod-receiver element defining a channel having an open top such that at least a portion of the rod may be inserted into the channel by moving the rod in a first sagittal plane, the rod-receiver element being rotatable 360 degrees in predetermined angular increments in place relative to the extension element to adjust and fix the direction of extension of the at least a portion of the rod in a first coronal plane; and
a clip member comprising a pair of legs coupled by a connecting portion, the clip member being disposed between the arms such that the connecting portion is flush with a bottom surface of the ring portion that is opposite the upper surface of the clip member and the clip member is secured to the ring portion, wherein the at least a portion of the rod engages the rod-receiver element when the rod extends within the vicinity of the spinal system and the bone structure.

17. The apparatus of claim 16 wherein the legs are biased away from one another.

18. The apparatus of claim 17 further comprising a washer disposed between the rod receiver element and the ring portion of the extension element wherein the at least a portion of the rod engages the washer when the at least a portion of the rod is inserted into the channel.

19. The apparatus of claim 18 wherein the washer is fixed relative to the rod receiver element such that the washer is rotatable with the rod receiver element relative to the extension element;

wherein a first plurality of teeth is formed in the washer and is adapted to mesh with the teeth formed in the ring portion to lock the direction of extension of the at least a portion of the rod in the first coronal plane when the at least a portion of the rod is into the channel by moving the rod in a first sagittal plane; and wherein a spacing between each pair of adjacent teeth in the first plurality of teeth defines each corresponding predetermined angular increment.

20. The apparatus of claim 19 further comprising a second fastener threadably engaged with the rod-receiver element for preventing relative movement between the at least a portion of the rod and the rod-receiver element, the second fastener configured to contact the at least a portion of the rod so that the at least a portion of the rod bears against the washer to lock the direction of extension of the at least a portion of the rod in the first coronal plane.

* * * * *